(12) United States Patent
Morikawa et al.

(10) Patent No.: US 11,634,660 B2
(45) Date of Patent: Apr. 25, 2023

(54) DETERGENT COMPOSITION FOR TEXTILE PRODUCTS

(71) Applicant: Kao Corporation, Tokyo (JP)

(72) Inventors: Satoshi Morikawa, Wakayama (JP); Ayako Ishihara, Tokyo (JP)

(73) Assignee: KAO CORPORATION, Tokyo (JP)

( * ) Notice: Subject to any disclaimer, the term of this patent is extended or adjusted under 35 U.S.C. 154(b) by 38 days.

(21) Appl. No.: 16/638,919

(22) PCT Filed: Sep. 5, 2018

(86) PCT No.: PCT/JP2018/032892
§ 371 (c)(1),
(2) Date: Feb. 13, 2020

(87) PCT Pub. No.: WO2019/049895
PCT Pub. Date: Mar. 14, 2019

(65) Prior Publication Data
US 2020/0190432 A1 Jun. 18, 2020

(30) Foreign Application Priority Data
Sep. 6, 2017 (JP) .............................. JP2017-171537

(51) Int. Cl.
C11D 1/00 (2006.01)
C11D 1/37 (2006.01)
C11D 11/00 (2006.01)
C11D 1/12 (2006.01)
C11D 1/14 (2006.01)

(52) U.S. Cl.
CPC ............ *C11D 1/37* (2013.01); *C11D 11/0017* (2013.01); *C11D 1/12* (2013.01); *C11D 1/14* (2013.01)

(58) Field of Classification Search
CPC .......... C11D 1/37; C11D 11/0017; C11D 1/14
See application file for complete search history.

(56) References Cited

U.S. PATENT DOCUMENTS

| | | | |
|---|---|---|---|
| 3,332,880 A | 7/1967 | Kessler et al. | |
| 3,428,654 A | 2/1969 | Rubinfeld et al. | |
| 5,078,916 A * | 1/1992 | Kok ....................... | C11D 1/143 510/488 |
| 2015/0202134 A1* | 7/2015 | Yoshikawa ............ | A61K 8/466 510/127 |
| 2015/0275133 A1* | 10/2015 | Doi ......................... | A61Q 5/02 510/127 |
| 2016/0000678 A1 | 1/2016 | Yoshikawa et al. | |
| 2016/0332961 A1 | 11/2016 | Hori et al. | |
| 2018/0371360 A1 | 12/2018 | Doi | |
| 2019/0169536 A1 | 6/2019 | Tabuchi et al. | |
| 2020/0318032 A1* | 10/2020 | Yamada ................ | C11D 17/08 |

FOREIGN PATENT DOCUMENTS

| | | |
|---|---|---|
| CN | 109563440 A | 4/2019 |
| EP | 0 050 897 A1 | 5/1982 |
| EP | 0 377 261 A2 | 7/1990 |
| EP | 2 899 258 A1 | 7/2015 |
| EP | 2 952 567 A1 | 12/2015 |
| EP | 3 388 051 A1 | 10/2018 |
| GB | 2 236 538 A | 4/1991 |
| JP | 60-96692 A | 5/1985 |
| JP | 60-96693 A | 5/1985 |
| JP | 62-72795 A | 4/1987 |
| JP | 3-126793 A | 5/1991 |
| JP | 6-316700 A | 11/1994 |
| JP | 2003-73697 A | 3/2003 |
| JP | 2003-81935 A | 3/2003 |
| JP | 2008-156590 A | 7/2008 |
| JP | 2014-76988 A | 5/2014 |
| JP | 2014-77126 A | 5/2014 |
| JP | 2014-167108 A | 9/2014 |
| JP | 2015-27977 A | 2/2015 |
| JP | 2015-143203 A | 8/2015 |
| WO | WO 2016/160407 A1 | 10/2016 |
| WO | WO 2017/098639 A1 | 6/2017 |
| WO | WO 2017/100051 A2 | 6/2017 |
| WO | WO 2018/030328 A1 | 2/2018 |

OTHER PUBLICATIONS

Extended European Search Report for European Application No. 18854027.2, dated Apr. 21, 2021.
Chinese Notification of First Office Action and Search Report (including an English traslation thereof) issued in the corresponding Chinese Patent Application No. 201880053546.X dated Oct. 12, 2020.
International Preliminary Report on Patentability and English translation of the Written Opinion of the International Searching Authority, dated Mar. 19, 2020, for International Application No. PCT/JP2018/032892.
International Search Report (PCT/ISA/210) issued in PCT/JP2018/032892, dated Nov. 20, 2018.
Stapersma et al., "Hydroxy Alkane Sulfonate (HAS), a New Surfactant Based on Olefins," J. Am. Oil Chem. Soc., vol. 69, No. 1, Jan. 1992, pp. 39-43.
Russian Office Action and Search Report for Russian Application No. 2020112282, dated Jul. 1, 2021, with an English translation.
Japanese Office Action for Japanese Application No. 2018-166086, dated Mar. 22, 2022.

\* cited by examiner

*Primary Examiner* — Necholus Ogden, Jr.
(74) *Attorney, Agent, or Firm* — Birch, Stewart, Kolasch & Birch, LLP

(57) ABSTRACT

The present invention provides a detergent composition for textile products, containing the following component (A) and component (B):
   component (A): an internal olefin sulfonate having 16 or more and 18 or less carbons; and
   component (B): an alkyl sulfate having 12 or more and 14 or less carbons.

11 Claims, No Drawings

DETERGENT COMPOSITION FOR TEXTILE PRODUCTS

FIELD OF THE INVENTION

The present invention relates to a detergent composition for textile products, a method for cleaning a textile product, and a method for producing a detergent composition for textile products.

BACKGROUND OF THE INVENTION

Anionic surfactants, particularly alkylbenzene sulfonates, olefin sulfonates, and further, internal olefin sulfonates obtained using as a raw material an internal olefin having a double bond not at the end of the olefin chain but inside the olefin chain, and nonionic surfactants containing an oxyalkylene group having 2 to 3 carbons have been heretofore widely used as household and industrial detergent components.

JP-A 2014-077126 and JP-A 2014-076988 disclose an internal olefin sulfonate having a specific number of carbons, and a detergent composition containing the internal olefin sulfate, and suggests that an alkyl sulfate may be used in combination.

JP-A 3-126793 discloses a detergent composition containing an internal olefin sulfonate and a specific nonionic surfactant at a specific ratio, the internal olefin sulfonate having a specific number of carbons.

EP-A 0377261 discloses a detergent composition which contains an internal olefin sulfonate containing a β-hydroxysulfonate in an amount of at least 25 mass % in the total amount of the sulfonate and having 8 to 26 carbons.

SUMMARY OF THE INVENTION

The present invention relates to a detergent composition for textile products which is excellent in cleaning properties on textile products. The present invention relates particularly to a detergent composition for textile products which is capable of maintaining a cleaning effect against stains on textile products even when water used for cleaning has high hardness.

The present invention relates to a detergent composition for textile products, containing the following component (A) and component (B):

component (A): an internal olefin sulfonate having 16 or more and 18 or less carbons; and component (B): one or more anionic surfactants selected from an alkyl sulfate having 12 or more and 14 or less carbons and an alkane sulfonate having 12 or more and 14 or less carbons.

The present invention also relates to a method for cleaning a textile product, including cleaning the textile product with a cleaning liquid in which the detergent composition for textile products according to the present invention is diluted with water.

The present invention also relates to a method for producing a detergent composition for textile products, including mixing the following component (A) and component (B).

According to the present invention, it is possible to obtain a detergent composition for textile products which is excellent in cleaning properties on textile products. In particular, it is possible to obtain a detergent composition for textile products which is capable of maintaining a cleaning effect against stains on textile products even when water used for cleaning has high hardness.

Embodiments of the Invention

<Component (A)>

Component (A) in the present invention is an internal olefin sulfonate having 16 or more and 18 or less carbons. By using component (A) in combination with component (B) which is one or more anionic surfactants selected from an alkyl sulfate having 12 or more and 14 or less carbons and an alkane sulfonate having 12 or more and 14 or less carbons, excellent cleaning properties against stains on textile products are exhibited.

The number of carbons of the internal olefin sulfonate in component (A) is 16 or more and 18 or less from the viewpoint of enhancing cleaning properties against stains on textile products. This carbon number is the number of carbons of the internal olefin sulfonic acid moiety which does not include the salt moiety in component (A).

Internal olefin sulfonates in component (A) also include those containing a very small amount of a so-called alfa-olefin sulfonate (hereinafter, also referred to as an α-olefin sulfonate) in which a double bond is present at position 1 in the carbon chain. Component (A) may contain an alfa-olefin sulfonate in an amount of up to 10 mass %. The content of the alfa-olefin sulfonate is preferably 7 mass % or less, more preferably 5 mass % or less, further preferably 3 mass % or less from the viewpoint of further enhancing cleaning properties against stains on textile products, and preferably 0.01 mass % or more from the viewpoint of reduction of production costs and improving productivity.

When the internal olefin is subjected to sulfonation, β-sultone is quantitatively generated, and β-sultone is partially changed into γ-sultone and an olefin sulfonic acid, which are further converted into a hydroxyalkane sulfonate and an olefin sulfonate in neutralization and hydrolysis steps (e.g. J. Am. Oil Chem. Soc. 69, 39(1992)). Here, the hydroxy group of the resulting hydroxyalkane sulfonate is present inside the alkane chain, and the double bond of the olefin sulfonate is present inside the olefin chain. The resulting products are mainly mixtures of these sulfonates, some of which may contain a very small amount of a hydroxyalkane sulfonate having a hydroxy group at the end of the carbon chain, or an olefin sulfonate having a double bond at the end of the carbon chain.

Herein, the products and mixtures thereof are referred to collectively as an internal olefin sulfonate (component (A)). The hydroxyalkane sulfonate is referred to as a hydroxy form of internal olefin sulfonate (hereinafter, also referred to as HAS), and the olefin sulfonate is referred to as an olefin form of internal olefin sulfonate (hereinafter, also referred to as IOS).

The mass ratio of compounds in component (A) can be measured by a high performance liquid chromatography-mass spectrometer (hereinafter, abbreviated as HPLC-MS). Specifically, the mass ratio can be determined from HPLC-MS peak areas in component (A).

Examples of the salts in the internal olefin sulfonate include alkali metal salts, alkaline earth metal (½ atom) salts, ammonium salts and organic ammonium salts. Examples of the alkali metal salts include sodium salts and potassium salts. Examples of the organic ammonium salts include alkanolammonium salts having 1 or more and 6 or less carbons.

From the viewpoint of further enhancing cleaning properties against stains on textile products by using component (A) of the present invention in combination with component (B), component (A) is an internal olefin sulfonate having 16 or more and 18 or less carbons and, in the internal olefin sulfonate, a mass ratio of an internal olefin sulfonate having the sulfonate group at position 2 or higher and 4 or lower and having 16 or more and 18 or less carbons (IO-1S) to an internal olefin sulfonate having the sulfonate group at position 5 or higher and having 16 or more and 18 or less carbons (IO-2S), (IO-1S)/(IO-2S), is preferably 0.75 or more, more preferably 0.9 or more, further preferably 1.0 or more, furthermore preferably 1.2 or more, furthermore preferably 1.4 or more, furthermore preferably 1.6 or more, furthermore preferably 2.0 or more, furthermore preferably 2.4 or more, furthermore preferably 4.5 or more, and preferably 5.5 or less.

The contents of the compounds different in position of the sulfonate group in component (A) can be measured by HPLC-MS. The contents of the compounds different in position of the sulfonate group herein are determined as a mass ratio based on the HPLC-MS peak areas for the compounds having sulfonate groups at respective positions in all HASs in component (A).

Here, the HAS refers to hydroxyalkane sulfonates among compounds generated by sulfonation of internal olefin sulfonic acids, i.e. hydroxy forms of internal olefin sulfonates.

In the present invention, the internal olefin sulfonate having the sulfonate group at position 2 or higher and 4 or lower and having 16 or more and 18 or less carbons (IO-1S) means a sulfonate having the sulfonate group at position 2 or higher and 4 or lower and having 16 or more and 18 or less carbons in a HAS form having 16 or more and 18 or less carbons.

In addition, the internal olefin sulfonate having the sulfonate group at position 5 or higher and having 16 or more and 18 or less carbons (IO-2S) means a sulfonate having the sulfonate group at position 5 or higher and having 16 or more and 18 or less carbons in a HAS form having 16 or more and 18 or less carbons.

The internal olefin sulfonate which is component (A) is composed by including the internal olefin sulfonate having the sulfonate group at position 2 or higher and 4 or lower and having 16 or more and 18 or less carbons (IO-1S) and the internal olefin sulfonate having the sulfonate group at position 5 or higher and having 16 or more and 18 or less carbons (IO-2S). The maximum value of the binding position of the sulfonate group in the internal olefin sulfonate (IO-2S) varies depending on the number of carbons.

The mass ratio (IO-1S)/(IO-2S) for component (A) is dictated by component (A) that is ultimately obtained. For example, even an internal olefin sulfonate obtained by mixing an internal olefin sulfonate in which the mass ratio (IO-1S)/(IO-2S) is out of the above range is deemed as an internal olefin sulfonate of component (A) when the mass ratio (IO-1S)/(IO-2S) in the composition of the internal olefin sulfonate is within the above range.

For the mass of component (A), sulfonate (IO-1S) or sulfonate (IO-2S), a value calculated based on the form of sodium ions in place of counterions is used.

<Component (B)>

Component (B) is one or more anionic surfactants selected from an alkyl sulfate having 12 or more and 14 or less carbons and an alkane sulfonate having 12 or more and 14 or less carbons. By using component (B) in combination with component (A) which is an internal olefin sulfonate having 16 or more and 18 or less carbons, cleaning properties against stains on textile products can be enhanced. In addition, cleaning properties against stains on textile products can be maintained even when water used for cleaning textile products has high hardness. The number of carbons of component (B) is the number of carbons of the alkyl sulfuric acid or alkane sulfonic acid moiety which does not include the salt moiety in component (B). In the present invention, it is assumed that the cleaning effect of component (A) can be further enhanced in a synergistic manner by forming a surfactant structure suitable for cleaning in a cleaning liquid because component (A) which is an internal olefin sulfonate having 16 or more and 18 or less carbons has a hydrophilic group inside the hydrocarbon group, and with respect to the binding position of the sulfonate group as a hydrophilic group, the length of the longest hydrocarbon group is about 12 to 14 carbons, and hence almost equal to the number of carbons of component (B). In this respect, component (B) is preferably an anionic surfactant in which the carbon atom binding with a sulfate group or a sulfonate group is a primary carbon atom.

Component (B) is preferably one or more anionic surfactants selected from an alkyl sulfate having 12 carbons and an alkane sulfonate having 12 carbons. From the viewpoint of ensuring that cleaning properties can be enhanced by using component (B) in combination with component (A), the content of one or more anionic surfactants selected from an alkyl sulfate having 12 carbons and an alkane sulfonate having 12 carbons in whole component (B) contained in the detergent composition for textile products according to the present invention is preferably 50 mass % or more, more preferably 60 mass % or more, further preferably 70 mass % or more, furthermore preferably 80 mass % or more, and 100 mass % or less.

Examples of the salt forming component (B) include alkali metal salts such as sodium salts and potassium salts, alkanolamine salts, and alkaline earth salts such as magnesium salts and calcium salts.

For the mass of component (B), a value calculated based on the form of sodium ions in place of counterions is used.

<Fiber>

The fiber forming a textile product to be cleaned with the detergent composition for textile products according to the present invention may be either hydrophobic fiber or hydrophilic fiber. Examples of the hydrophobic fiber include protein-based fiber (milk protein casein fiber, promix, etc.), polyamide-based fiber (nylon etc.), polyester-based fiber (polyester etc.), polyacrylonitrile-based fiber (acrylic etc.), polyvinyl alcohol-based fiber (vinylon etc.), polyvinyl chloride-based fiber (polyvinyl chloride etc.), polyvinylidene chloride-base fiber (vinylidene etc.), polyolefin-based fiber (polyethylene, polypropylene, etc.), polyurethane-based fiber (polyurethane etc.), polyvinyl chloride/polyvinyl alcohol copolymer-based fiber (polychlal etc.), polyalkylene paraoxybenzoate-based fiber (benzoate etc.), polyfluoroethylene-based fiber (polytetrafluoroethylene etc.), glass fiber, carbon fiber, alumina fiber, silicon carbide fiber, rock fiber, slag fiber and metal fiber (gold thread, silver thread, steel fiber, etc.). Examples of the hydrophilic fiber include seed hair fiber (cotton, arboreous cotton, kapok, etc.), bast fiber (hemp, flax, ramie, India hemp, jute, etc.), vein fiber (Manila hemp, sisal hemp, etc.), palm fiber, rushes, straw, animal hair fiber (wool, mohair, cashmere, camel hair, alpaca, vicuna, angora, etc.), silk fiber (house silkworm silk, wild silkworm silk, etc.), feathers and cellulose-based fiber (rayon, polynosic, cupra, acetate, etc.).

The fiber is preferably fiber including arboreous cotton.

<Textile Product>

In the present invention, the textile product means fabrics such as woven fabrics, knitted fabrics and nonwoven fabrics using the hydrophobic fiber or the hydrophilic fiber, and products obtained by using the same, such as undershirts, T-shirts, shirts, blouses, slacks, hats, handkerchiefs, towels, knitted garments, socks, underwear, tights, etc.

<Composition Etc.>

The total of the content of component (A) and the content of component (B) in the detergent composition for textile products according to the present invention is preferably 1 mass % or more, more preferably 3 mass % or more, further preferably 5 mass % or more, furthermore preferably 7 mass % or more, furthermore preferably 10 mass % or more from the viewpoint of further enhancing the cleaning properties per mass of the detergent composition for textile products in cleaning of textiles, and preferably 50 mass % or less, more preferably 40 mass % or less, further preferably 30 mass % or less from the viewpoint of further enhancing cleaning properties against stains on textile products even when the detergent composition for textile products according to the present invention is used for cleaning at a low temperature.

The content of component (A) or component (B) contained in the detergent composition for textile products is based on a value calculated based on the form of sodium ions in place of counterions. That is, the content is calculated based on the form of sodium salts.

In the present invention, the proportion of the total amount of component (A) and component (B) in all surfactants contained in the detergent composition for textile products is 50 mass % or more, or even 60 mass % or more, or even 70 mass % or more, or even 80 mass % or more, and preferably 100 mass % or less, or may be 100 mass %.

In the present invention, the proportion of the total amount of component (A) and component (B) in all anionic surfactants contained in the detergent composition for textile products is 50 mass % or more, or even 60 mass % or more, or even 70 mass % or more, or even 80 mass % or more, and preferably 100 mass % or less, or may be 100 mass %.

In the detergent composition for textile products of the present invention, from the viewpoint of ensuring that cleaning properties on textile products can be further enhanced by using component (A) and component (B) in combination, the mass ratio of the content of component (B) to the content of component (A), (B)/(A), is preferably 0.1 or more, more preferably 0.2 or more, further preferably 0.25 or more, furthermore preferably 0.3 or more, furthermore preferably 0.4 or more, furthermore preferably 0.5 or more, furthermore preferably 0.6 or more, and preferably 15 or less, more preferably 10 or less, further preferably 9 or less, furthermore preferably 8 or less, furthermore preferably 7 or less, furthermore preferably 6 or less, furthermore preferably 5 or less, furthermore preferably 4.5 or less, furthermore preferably 4 or less, furthermore preferably 3.5 or less, furthermore preferably 3 or less.

<Optional Components>

For the detergent composition for textile products according to the present invention, a surfactant other than component (A) and component (B) can be used as component (C) as long as the effect of the present invention is not hindered. Examples of component (C) include one or more surfactants selected from an anionic surfactant other than component (A) and component (B), and a nonionic surfactant.

Examples of component (C) include one or more anionic surfactants selected from the following component (c1), component (c2) and component (c3):

component (c1): a polyoxyalkylene alkyl ether sulfate or a polyoxyalkylene alkenyl ether sulfate;

component (c2): an anionic surfactant having a sulfonate group (except for component (A) and component (B)); and component (c3): a fatty acid or a salt thereof.

More specific examples of component (c1) include one or more anionic surfactants selected from a polyoxyalkylene alkyl sulfate in which the number of carbons of the alkyl group is 10 or more and 18 or less and the average number of added moles of the alkylene oxide is 1 or more and 3 or less, and a polyoxyalkylene alkenyl ether sulfate in which the number of carbons of the alkenyl group is 10 or more and 18 or less and the average number of added moles of the alkylene oxide is 1 or more and 3 or less. Further, sodium salts thereof are further preferable.

Component (c2) which is an anionic surfactant having a sulfonate group is an anionic surfactant having a sulfonate as a hydrophilic group (except for component (A) and component (B)).

More specific examples of component (c2) include one or more anionic surfactants selected from an alkylbenzene sulfonate in which the number of carbons of the alkyl group is 10 or more and 18 or less, an alkenylbenzene sulfonate in which the number of carbons of the alkenyl group is 10 or more and 18 or less, an α-olefin sulfonate in which the number of carbons of the α-olefin moiety is 10 or more and 14 or less, an α-sulfofatty acid salt in which the number of carbons of the fatty acid moiety is 10 or more and 18 or less, an α-sulfofatty acid lower alkyl ester salt in which the number of carbons of the fatty acid moiety is 10 or more and 18 or less and the number of carbons of the ester moiety is 1 or more and 5 or less, and an internal olefin sulfonate having 12 or more and 14 or less carbons.

Examples of component (c3) which is a fatty acid or a salt thereof include fatty acids having 10 or more and 20 or less carbons, or salts thereof. From the viewpoint of further enhancing cleaning properties against stains on textile products by component (A), the number of carbons of component (c3) is 10 or more, preferably 12 or more, more preferably 14 or more, and 20 or less, preferably 18 or less.

The salts as anionic surfactants which are components (c1) to (c3) are preferably alkali metal salts, more preferably sodium salts or potassium salts, further preferably sodium salts.

Examples of other components (C) include component (c4) which is a nonionic surfactant having a hydroxyl group or a polyoxyalkylene group.

The content of component (C) in the detergent composition for textile products according to the present invention is preferably 30 mass % or less, more preferably 20 mass % or less, or may be 0 mass %. In addition, the proportion of the total amount of component (A) and component (B) in all anionic surfactants is preferably within the above predetermined range.

In addition, the following components (d1) to (d7) may be blended in the detergent composition for textile products according to the present invention:

(d1) a re-contamination inhibitor and dispersant such as polyacrylic acid, polymaleic acid or carboxymethylcellulose in an amount of 0.01 mass % or more and 10 mass % or less in the composition;

(d2) a bleaching agent such as hydrogen peroxide, sodium percarbonate or sodium perborate in an amount of 0.01 mass % or more and 10 mass % or less in the composition;

(d3) a bleaching activator such as tetraacetylethylenediamine or a bleaching activator represented by any of general formulae (I-2) to (I-7) in JP-A 6-316700, in an amount of 0.01 mass % or more and 10 mass % or less in the composition;

(d4) one or more enzymes selected from cellulase, amylase, pectinase, protease and lipase, preferably one or more enzymes selected from amylase and protease, in an amount of 0.001 mass % or more, preferably 0.01 mass % or more, more preferably 0.1 mass % or more, further preferably 0.3 mass % or more, and 2 mass % or less, preferably 1 mass % or less in the composition;

(d5) a fluorescent dye, e.g. a fluorescent dye commercially available as Tinopal CBS (trade name, manufactured by Ciba Specialty Chemicals Inc.) or WHITEX SA (trade name, manufactured by Sumitomo Chemical Company, Limited), in an amount of 0.001 mass % or more and 1 mass % or less in the composition;

(d6) an antioxidant such as butylhydroxytoluene, distyrenated cresol, sodium sulfite or sodium hydrogensulfite in an amount of 0.01 mass % or more and 2 mass % or less in the composition; and (d7) an appropriate amount of a pigment, a perfume, an antiseptic and/or a defoaming agent such as silicone.

<Water>

The detergent composition for textile products according to the present invention may contain water. For example, the detergent composition may contain water for ensuring that the composition of the present invention is in a liquid form at 4° C. or higher and 40° C. or lower. Deionized water (sometimes referred to as ion-exchanged water) or water obtained by adding sodium hypochlorite to ion-exchanged water in an amount of 1 mg/kg or more and 5 mg/kg or less may be used. Also, tap water may be used.

The content of water in the detergent composition for textile products according to the present invention is preferably 10 mass % or more, more preferably 15 mass % or more, and preferably 97 mass % or less, more preferably 95 mass % or less.

When the detergent composition for textile products according to the present invention is a liquid containing water, the pH of the composition at 20° C. is preferably 3 or more, more preferably 4 or more, and preferably 10 or less, more preferably 9 or less, further preferably 8 or less. The pH is measured in accordance with the pH measurement method described below.

<pH Measurement Method>

A pH measuring composite electrode (manufactured by HORIBA, Ltd., glass-laminated sleeve type) is connected to a pH meter (pH/Ion Meter F-23 manufactured by HORIBA, Ltd.), and the pH meter is powered on. As a liquid in the pH electrode, a saturated aqueous potassium chloride solution (3.33 mol/L) is used. Next, 100 mL beakers are filled with a pH 4.01 standard solution (phthalate standard solution), a pH 6.86 standard solution (neutral phosphate standard solution) and a pH 9.18 standard solution (borate standard solution), respectively, and immersed in a thermostatic bath at 25° C. for 30 minutes. The pH measuring electrode is immersed for 3 minutes in the standard solutions adjusted to a constant temperature, and calibrated to pH 6.86, then to pH 9.18 and then to pH 4.01. A sample to be measured is adjusted to 25° C., the electrode of the pH meter is immersed in the sample, and the pH is measured after 1 minute.

The detergent composition for textile products according to the present invention can be produced by mixing component (A) and component (B).

The present invention also relates to a method for cleaning a textile product, including cleaning a textile product with the detergent composition for textile products according to the present invention. In this method, it is preferable to clean a textile product with a cleaning liquid in which the detergent composition for textile products according to the present invention is diluted with water. The matters described for the detergent composition for textile products according to the present invention can be appropriately applied to the method for cleaning a textile product according to the present invention. The total concentration of component (A) and component (B) in the cleaning liquid is preferably 0.001 mass % or more, more preferably 0.002 mass % or more, further preferably 0.003 mass % or more, and preferably 0.1 mass % or less, more preferably 0.05 mass % or less, further preferably 0.03 mass % or less. The mass ratio of component (B) to component (A), (B)/(A), in the cleaning liquid can be selected from the range described for the detergent composition for textile products according to the present invention. The pH of the cleaning liquid is preferably 5 or more, more preferably 6 or more, further preferably 7 or more, and preferably 10 or less, more preferably 9 or less, further preferably 8 or less. The pH is a pH at a temperature in cleaning. The pH may also be a pH at 20° C. The pH of the cleaning liquid can be measured by the pH measurement method described for the detergent composition for textile products. As the textile product, a textile product with sebum stains can be targeted.

From the viewpoint of securing the effect of the present invention, the water for diluting the detergent composition for textile products according to the present invention in the method for cleaning a textile product according to the present invention is preferably water containing hard components such as calcium and magnesium. From the viewpoint of ensuring that by using component (A) and component (B) in combination, cleaning properties can be enhanced even when the hardness is high, the hardness of water is preferably 1° dH or more, more preferably 4° dH or more, further preferably 5° dH or more, furthermore preferably 6° dH or more, and preferably 20° dH or less, more preferably 18° dH or less, further preferably 15° dH or less, furthermore preferably 15° dH or less, in terms of German hardness. The water includes water used for preparation of the cleaning liquid, rinsing and the like.

The German hardness (° dH) herein refers to a concentration of calcium and magnesium in water, which is expressed, in terms of $CaCO_3$, in accordance with the equation: 1 mg/L (ppm)=about 0.056° dH (1° dH=17.8 ppm).

The concentration of calcium and magnesium for German hardness can be determined by chelate titration using disodium ethylenediaminetetraacetate. A specific method for measuring the German hardness of water will be described below.

<Method for Measuring German Hardness of Water>

[Reagent]

0.01 mol/l EDTA.2Na solution: a 0.01 mol/l aqueous solution of disodium ethylenediaminetetraacetate (titrating solution, 0.01 M EDTA-Na$_2$, manufactured by Sigma-Aldrich Co. LLC)

Universal BT indicator (product name: Universal BT, manufactured by DOJINDO LABORATORIES)

Hardness measuring ammonia buffer solution (a solution obtained by dissolving 67.5 g of ammonium chloride in 570 ml of 28 w/v % aqueous ammonia, and diluting the solution to a total volume of 1000 ml with ion-exchanged water)

[Measurement of Hardness]

(1) 20 ml of water as a sample is taken into conical beaker with a transfer pipet.

(2) 2 ml of the hardness measuring ammonia buffer solution is added.

(3) 0.5 ml of the Universal BT indicator is added. The solution after the addition is checked and confirmed to exhibit a purple-red color.

(4) The 0.01 mol/l EDTA.2Na solution is added dropwise from a burette while the conical beaker is thoroughly shaken, and the point at which the water as a sample turns blue in color is defined as an end point.

(5) The total hardness is determined from the following calculation formula.

$$\text{hardness (° dH)} = T \times 0.01 \times F \times 56.0774 \times 100/A$$

T: titer of 0.01 mol/l EDTA.2Na solution (mL)
A: sample volume (20 mL, volume of water as sample)
F: factor of 0.01 mol/l EDTA.2Na solution <Method for Improving Resistance to Hardness>

In the detergent composition for textile products according to the present invention, component (A) and component (B) are used in combination, and thus even when water used for cleaning has high hardness, cleaning properties can be enhanced as compared to the cleaning properties of component (A) or component (B) alone.

The present invention provides a method for improving the resistance to hardness of a detergent composition for textile products, including using component (A) and component (B) in combination.

The present invention also provides a method for improving the resistance to hardness of a detergent composition for textile products which contains a surfactant, including using component (A) and component (B) in combination as the surfactant. Here, the proportion of component (A) and component (B) in all surfactants is 50 mass % or more, or even 60 mass % or more, or even 70 mass % or more, or even 80 mass % or more, and preferably 100 mass % or less, or may be 100 mass %.

The matters described for the detergent composition for textile products according to the present invention can be appropriately applied to the method for improving the resistance to hardness according to the present invention.

Hereinafter, the aspects of the present invention will be shown. The matters described for the detergent composition for textile products according to the present invention can be appropriately applied to these aspects.

<1>

A detergent composition for textile products, containing the following component (A) and component (B):

component (A): an internal olefin sulfonate having 16 or more and 18 or less carbons; and component (B): one or more anionic surfactants selected from an alkyl sulfate having 12 or more and 14 or less carbons and an alkane sulfonate having 12 or more and 14 or less carbons.

<2>

The detergent composition for textile products according to <1>, wherein component (A) is an internal olefin sulfonate having 16 or more and 18 or less carbons and, in the internal olefin sulfonate, a mass ratio of an internal olefin sulfonate having the sulfonate group at position 2 or higher and 4 or lower and having 16 or more and 18 or less carbons (IO-1S) to an internal olefin sulfonate having the sulfonate group at position 5 or higher and having 16 or more and 18 or less carbons (IO-2S), (IO-1S)/(IO-2S), is 0.75 or more and 5.5 or less.

<3>

The detergent composition for textile products according to <1> or <2>, wherein component (A) is an internal olefin sulfonate having 16 or more and 18 or less carbons and, in the internal olefin sulfonate, a mass ratio of an internal olefin sulfonate having the sulfonate group at position 2 or higher and 4 or lower and having 16 or more and 18 or less carbons (IO-1S) to an internal olefin sulfonate having the sulfonate group at position 5 or higher and having 16 or more and 18 or less carbons (IO-2S), (IO-1S)/(IO-2S), is 0.9 or more, preferably 1.0 or more, more preferably 1.2 or more, further preferably 1.4 or more, furthermore preferably 1.6 or more, furthermore preferably 2.0 or more, furthermore preferably 2.4 or more, furthermore preferably 4.5 or more, and 5.5 or less.

<4>

The detergent composition for textile products according to any one of <1> to <3>, wherein the content of an alfa-olefin sulfonate in component (A) is 10 mass % or less, preferably 7 mass % or less, more preferably 5 mass % or less, further preferably 3 mass % or less, and 0.01 mass % or more.

<5>

The detergent composition for textile products according to any one of <1> to <4>, wherein the salt as component (A) is an alkali metal salt, an alkaline earth metal (½ atom) salt, an ammonium salt or an organic ammonium salt.

<6>

The detergent composition for textile products according to <5>, wherein the alkali metal salt is a sodium salt or a potassium salt, and the organic ammonium salt is an alkanolammonium salt having 1 or more and 6 or less carbons.

<7>

The detergent composition for textile products according to any one of <1> to <6>, wherein the content of one or more anionic surfactants selected from an alkyl sulfate having 12 carbons and an alkane sulfonate having 12 carbons in whole component (B) contained in the detergent composition for textile products is preferably 50 mass % or more and 100 mass % or less.

<8>

The detergent composition for textile products according to any one of <1> to <7>, wherein the content of one or more anionic surfactants selected from an alkyl sulfate having 12 carbons and an alkane sulfonate having 12 carbons in whole component (B) contained in the detergent composition for textile products is 60 mass % or more, preferably 70 mass % or more, more preferably 80 mass % or more, and 100 mass % or less.

<9>

The detergent composition for textile products according to any one of <1> to <8>, wherein the salt as component (B) is an alkali metal salt such as a sodium salt or a potassium salt, an alkanolamine salt, or an alkaline earth metal salt such as a magnesium salt or a calcium salt.

<10>

The detergent composition for textile products according to any one of <1> to <9>, wherein the mass ratio of the content of component (B) to the content of component (A), (B)/(A), is 0.1 or more and 15 or less.

<11>

The detergent composition for textile products according to any one of <1> to <10>, wherein the mass ratio of the content of component (B) to the content of component (A), (B)/(A), is 0.2 or more, preferably 0.25 or more, more preferably 0.3 or more, furthermore preferably 0.4 or more, furthermore preferably 0.5 or more, furthermore preferably 0.6 or more, and 10 or less, preferably 5 or less, more preferably 4.5 or less, further preferably 4 or less, furthermore preferably 3.5 or less, furthermore preferably 3 or less.

<12>

The detergent composition for textile products according to any one of <1> to <11>, wherein the content of an internal olefin sulfonate having 16 carbons in component (A) is 0 mass % or more and 80 mass % or less.

<13>

The detergent composition for textile products according to any one of <1> to <12>, wherein the proportion of the total amount of component (A) and component (B) in all surfactants contained in the detergent composition for textile products is 50 mass % or more, or even 60 mass % or more, or even 70 mass % or more, or even 80 mass % or more, and 100 mass % or less.

<14>

The detergent composition for textile products according to any one of <1> to <13>, wherein the proportion of the total amount of component (A) and component (B) in all anionic surfactants contained in the detergent composition for textile products is 50 mass % or more and 100 mass % or less.

<15>

The detergent composition for textile products according to any one of <1> to <14>, wherein the proportion of the total amount of component (A) and component (B) in all anionic surfactants contained in the detergent composition for textile products is 60 mass % or more, or even 70 mass % or more, or even 80 mass % or more, and 100 mass % or less.

<16>

The detergent composition for textile products according to any one of <1> to <15>, wherein the content of water in the detergent composition for textile products is 10 mass % or more, preferably 15 mass % or more, and 97 mass % or less, preferably 95 mass % or less.

<17>

The detergent composition for textile products according to any one of <1> to <16>, wherein the detergent composition for textile products is a liquid containing water, and the pH of the composition at 20° C. is 3 or more, preferably 4 or more, and 10 or less, preferably 9 or less, more preferably 8 or less.

<18>

A method for cleaning a textile product, including cleaning the textile product with a cleaning liquid in which the detergent composition for textile products according to any one of <1> to <17> is diluted with water.

<19>

The method for cleaning a textile product according to <18>, wherein the total concentration of component (A) and component (B) in the cleaning liquid is 0.001 mass % or more, preferably 0.002 mass % or more, more preferably 0.003 mass % or more, and 0.1 mass % or less, preferably 0.05 mass % or less, more preferably 0.03 mass % or less.

<20>

The method for cleaning a textile product according to <18> or <19>, wherein the pH of the cleaning liquid at 20° C. is 5 or more, preferably 6 or more, more preferably 7 or more, and 10 or less, preferably 9 or less, more preferably 8 or less.

<21>

The method for cleaning a textile product according to any one of <18> to <20>, wherein the hardness of water for diluting the composition is 1° dH or more, preferably 4° dH or more, more preferably 5° dH or more, further preferably 6° dH or more, and 20° dH or less, preferably 18° dH or less, more preferably 15° dH or less, further preferably 15° dH or less, in terms of German hardness.

<22>

A method for producing a detergent composition for textile products, including mixing the following component (A) and component (B):

component (A): an internal olefin sulfonate having 16 or more and 18 or less carbons; and component (B): one or more anionic surfactants selected from an alkyl sulfate having 12 or more and 14 or less carbons and an alkane sulfonate having 12 or more and 14 or less carbons.

<23>

A method for improving the resistance to hardness of a detergent composition for textile products, including using the following component (A) and component (B) in combination:

component (A): an internal olefin sulfonate having 16 or more and 18 or less carbons; and component (B): one or more anionic surfactants selected from an alkyl sulfate having 12 or more and 14 or less carbons and an alkane sulfonate having 12 or more and 14 or less carbons.

<24>

A method for improving the resistance to hardness of a detergent composition for textile products which contains a surfactant, including using the following component (A) and component (B) in combination as the surfactant:

component (A): an internal olefin sulfonate having 16 or more and 18 or less carbons; and component (B): one or more anionic surfactants selected from an alkyl sulfate having 12 or more and 14 or less carbons and an alkane sulfonate having 12 or more and 14 or less carbons.

EXAMPLES

[Preparation of Internal Olefin Sulfonate]

Internal olefins as raw materials for component (A) or component (A') [comparative compound of component (A)] are as follows.

Internal Olefin A

Internal olefin A is an internal olefin having 16 carbons and obtained by reference to the method described in JP-A 2014-76988, Production Example C. The double bond distribution (mass ratio) of internal olefin A is shown below.

Double bond distribution of internal olefin A: 1-olefin/2-olefin/3-olefin/4-olefin/5-olefin/6-olefin/7-olefin/8-olefin=1.0/29.8/24.4/18.3/13.0/7.1/3.2/3.2

Internal Olefin B

Internal olefin B is an internal olefin having 18 carbons and obtained by reference to the method described in JP-A 2014-76988, Production Example. The double bond distribution (mass ratio) of internal olefin B is shown below.

Double bond distribution of internal olefin B: 1-olefin/2-olefin/3-olefin/4-olefin/5-olefin/6-olefin/7-olefin/8-olefin/9-olefin=2.3/25.7/21.6/19.1/12.3/8.0/5.4/2.8/2.8

Internal Olefin C

Internal olefin C as a raw material for component (A') is an internal olefin having 12 carbons and obtained by reference to the method described in JP-A 2014-167108, Production Example B. The double bond distribution (mass ratio) of internal olefin C is shown below.

Double bond distribution of internal olefin C: 1-olefin/2-olefin/3-olefin/4-olefin/5-olefin/6-olefin=0.5/33.1/23.6/21.2/15.0/6.6

Internal Olefin D

Internal olefin D is an internal olefin having 16 carbons and obtained by reference to the method described in JP-A 2014-76988, Production Example A. The double bond distribution (mass ratio) of internal olefin D is shown below.

Double bond distribution of internal olefin D: 1-olefin/2-olefin/3-olefin/4-olefin/5-olefin/6-olefin/7-olefin/8-olefin=0.4/15.3/13.8/15.2/18.4/15.1/10.9/10.9

The double bond distribution of the internal olefin was measured by gas chromatography (hereinafter, abbreviated as GC). Specifically, dimethyl disulfide was reacted with the internal olefin to obtain a dithioated derivative, and each component was separated by GC. Accordingly, the double bond distribution of the internal olefin was determined from the peak area of each component. In the olefin having 18 carbons, the internal olefin having a double bond at position 8 and the internal olefin having a double bond at position 9 cannot be structurally discriminated, and can be discriminated when subjected to sulfonation. Thus, a value obtained by dividing the amount of internal olefins having a double bond at position 8 by 2 is shown in each of the fields of positions 8 and 9 for the sake of convenience. Similarly, in the olefin having 16 carbons, a value obtained by dividing the amount of internal olefins having a double bond at position 7 by 2 is shown in each of the fields of positions 7 and 8 for the sake of convenience.

Apparatuses used for measurement, and analysis conditions are as follows. GC apparatus: "HP6890" (manufactured by Hewlett-Packard Company), Column: "Ultra-Alloy-1HT Capillary Column" (30 m×250 μm×0.15 μm, Frontier Laboratories Ltd.), Detector: (hydrogen flame ionization detector (FID)), Injection temperature: 300° C., Detector temperature: 350° C., He flow rate: 4.6 mL/min (3) Synthesis of Sulfonates (a-1), (a-2) and (a'-1)

Using internal olefins A to C, the following sodium internal olefin sulfonates were obtained by reference to the method described in JP-A 2014-76988, Production Example.

Here, an internal olefin sulfonate obtained with internal olefin A as a raw material was defined as (a-1), an internal olefin sulfonate obtained with internal olefin B as a raw material was defined as (a-2), an internal olefin sulfonate obtained with internal olefin C as a raw material was defined as (a'-1), and an internal olefin sulfonate obtained with internal olefin D as a raw material was defined as (a-3).

Details of the sodium internal olefin sulfonates are described below.

(a-1): Sodium Internal Olefin Sulfonate Obtained from Internal Olefin A

The mass ratio of hydroxy form (sodium hydroxyalkane sulfonate)/olefin form (sodium olefin sulfonate) in (a-1) is 83/17. The position-distribution-mass ratio of the sulfonate groups of the HAS forms in (a-1) is as follows: position 1/position 2/position 3/position 4/position 5/positions 6 to 9=1.6/31.5/25.1/24.7/10.3/6.8. The ratio (IO-1S)/(IO-2S) is 4.8.

(a-2): Sodium Internal Olefin Sulfonate Obtained from Internal Olefin B

The mass ratio of hydroxy form (sodium hydroxyalkane sulfonate)/olefin form (sodium olefin sulfonate) in (a-2) is 84/16. The position-distribution-mass ratio of the sulfonate groups of the HAS forms in (a-2) is as follows: position 1/position 2/position 3/position 4/position 5/positions 6 to 9=1.5/22.1/17.2/21.8/13.5/23.9. The ratio (IO-1S)/(IO-2S) is 1.6.

(a-3): Sodium Internal Olefin Sulfonate Obtained from Internal Olefin D

The mass ratio of hydroxy form (sodium hydroxyalkane sulfonate)/olefin form (sodium olefin sulfonate) in (a-3) is 86/14. The position-distribution-mass ratio of the sulfonate groups of the HAS forms in (a-3) is as follows: position 1/position 2/position 3/position 4/position 5/positions 6 to 9=0.6/13.1/11.5/17.9/17.1/39.8. The ratio (IO-1S)/(IO-2S) is 0.74.

(a'-1): Sodium Internal Olefin Sulfonate Obtained from Internal Olefin C

The mass ratio of hydroxy form (sodium hydroxyalkane sulfonate)/olefin form (sodium olefin sulfonate) in (a'-1) is 92/8.

The position distribution of the sulfonate groups of the HAS forms contained in each internal olefin sulfonate was measured by a liquid chromatography mass spectrometer (hereinafter, abbreviated as LC-MS). The internal olefin sulfonate having a double bond at position 6 or higher was not definitely fractionated because peaks overlapped. Apparatuses used for measurement, and analysis conditions are as follows.

[Measuring Instruments]
LC apparatus: "LC-20ASXR" (manufactured by Shimadzu Corporation)
LC-MS apparatus: "LCMS-2020" (manufactured by Shimadzu Corporation)
Column: ODS Hypersil (length: 250 mm, inner diameter: 4.6 mm, particle diameter: 3 μm, manufactured by Thermo Fisher Scientific)
Detector: ESI (−), m/z=349.15 (C18), 321.10 (C16), 293.05 (C14)
[Solvents]
Solvent A: 10 mM aqueous ammonium acetate
Solvent B: acetonitrile/water=95/5 solution with 10 mM ammonium acetate added
[Elution Conditions]
Gradient: solvent A 60%-solvent B 40% (0-15 min)→solvent A 30%-solvent B 70% (15.1-20 min)→solvent A 60%-solvent B 40% (20.1-30 min)
Flow rate: 0.5 ml/min
Column temperature: 40° C.
Injection amount: 5 μl
<Formulation Component>
[Component (A)]
(a-1): sodium internal olefin sulfonate obtained from internal olefin A
(a-2): sodium internal olefin sulfonate obtained from internal olefin B
(a-3): sodium internal olefin sulfonate obtained from internal olefin D
[Component (A')]
(a'-1): sodium internal olefin sulfonate obtained from internal olefin C
[Component (B)]
(b-1): sodium lauryl sulfate
(b-2): sodium myristyl sulfate
(b-3): sodium 1-dodecane sulfonate
[Component (B')]
(b'-1): sodium decyl sulfate Example 1 and Comparative Example 1

<Preparation of Liquid Detergent Compositions for Textile Products>

Liquid detergent compositions for textile products as shown in Table 1 were prepared using the above formulation components and ion-exchanged water, and evaluation was performed for the following items. The results are shown in Table 1.

Specifically, the liquid detergent compositions for textile products as shown in Table 1 were prepared in the following manner. A 5 cm-long Teflon (registered trademark) stirrer piece was put in a glass beaker with a capacity of 200 mL, and the mass of the beaker was measured. Next, 80 g of ion-exchanged water at 20° C., component (A) or component (A'), and component (B) or component (B') were put in the beaker, and the beaker was sealed on the upper side with Saran Wrap (registered trademark).

The beaker with the contents was placed in a water bath installed in a magnetic stirrer and kept at 60° C., and the contents were stirred at 100 r/min for 30 minutes within a temperature range of 60±2° C. in terms of a temperature of water in the water bath. Next, the water in the water bath was replaced by tap water at 5° C., and the beaker was cooled to 20° C. in terms of a temperature of the composition in the beaker. Next, Saran Wrap (registered trademark) was removed, ion-exchanged water was added so that the contents had a mass of 100 g, and stirring was performed again at 100 r/min for 30 minutes to obtain each of the liquid detergent compositions for textile products as shown in Table 1. In Comparative Examples in Table 1, the mass ratio of (B)/(A) is shown with component (A') and component (B') used in place, respectively, of component (A) and component (B). The pH (20° C.) of each of the liquid detergent compositions for textile products as shown in Table 1 was measured by the pH measurement method described herein, and the results showed that all the compositions had a pH of 7.0.

<Method for Evaluation of Cleaning Properties (Evaluation (I))>

(1) Preparation of Model Artificially Sebum-Stained Cloth

A model artificially sebum-stained cloth was prepared by applying a model artificially sebum-staining liquid of the following composition to a cloth. The application of the model artificially sebum-staining liquid to the cloth was carried out by printing the artificially staining liquid on the cloth using a gravure roll coater. The process for preparing the model artificially sebum-staining cloth by applying the model artificially sebum-staining liquid to the cloth was carried out with a cell capacity of the gravure roll of 58 cm$^3$/m$^2$, a coating speed of 1.0 m/min, a drying temperature of 100° C. and a drying time of 1 minute. Cotton 2003 (manufactured by Tanigashira Shoten K.K.) was used as the cloth. *The composition of the model artificially sebum-staining liquid: lauric acid: 0.4 mass %, myristic acid: 3.1 mass %, pentadecanoic acid: 2.3 mass %, palmitic acid: 6.2 mass %, heptadecanoic acid: 0.4 mass %, stearic acid: 1.6 mass %, oleic acid: 7.8 mass %, trioleic acid: 13.0 mass %, n-hexadecyl palmitate: 2.2 mass %, squalene: 6.5 mass %, egg white lecithin liquid crystal substance: 1.9 mass %, Kanuma reddish soil: 8.1 mass %, carbon black: 0.01 mass %, and water: balance (total: 100 mass %).

(2) Measurement of Cleaning Ratio

Five model artificially sebum-stained cloths (6 cm×6 cm) prepared as described above were cleaned at 85 rpm for 10 minutes with a tergotometer (Ueshima, MS-8212). The cloths were each cleaned under the following conditions: water was injected so that the concentration of the liquid detergent composition for textile products as shown in Table 1 was 0.033 mass % (the water was prepared using ion-exchanged water, calcium chloride and magnesium chloride with the Ca/Mg ratio set to 8/2 (mass ratio) so that the German hardness was 3.5° dH, and the temperature of the water was adjusted to 20° C.), and cleaning was performed at a water temperature of 20° C. The pH of the cleaning liquid was measured in accordance with the method for measuring the pH of the detergent composition for textile products according to the present invention, and the results showed that the pH (20° C.) was 7.0. After cleaning, the cloth was rinsed with city water (20° C.) for 3 minutes. Thereafter, the stained cloth after rinsing was subjected to water removal treatment for 1 minute using a twin-tub washing machine, and then left standing at 20° C. and 43% RH for 12 hours to be dried. The cleaning properties were evaluated based on the cleaning ratio. The cleaning ratio (%) was measured by the following method, and an average for the five cloths was determined. The results are shown in Table 1. The reflectivity at 550 nm of unstained original cloths and cloths before and after cleaning were measured by a color-difference meter (Z-300A manufactured by NIPPON DENSHOKU INDUSTRIES Co., LTD.).

Cleaning ratio (%)=100×[(reflectivity after cleaning−reflectivity before cleaning)/(reflectivity of original cloth−reflectivity before cleaning)]

A cleaning ratio is compared against the cleaning ratio of Comparative Example 1-1, and when the value of the cleaning ratio is greater than that of Comparative Example 1-1, it can be determined that excellent detergency is exhibited. The liquid detergent compositions for textile products as described in Examples all had a cleaning ratio greater than that of the liquid detergent composition for textile products in Comparative Example 1-1. The greater the value of the cleaning ratio, the better.

TABLE 1

| | | | | Examples | | | | | | | | | |
|---|---|---|---|---|---|---|---|---|---|---|---|---|---|
| | | | | 1-1 | 1-2 | 1-3 | 1-4 | 1-5 | 1-6 | 1-7 | 1-8 | 1-9 | 1-10 |
| Liquid detergent compositions for textile products | Formulation compositions (mass %) | (A) | (a-1) | 8 | 6 | 4 | 2 | | | | 6 | 8 | 6 |
| | | | (a-2) | | | | | 6 | 4 | 2 | | | |
| | | | (a-3) | | | | | | | | | | |
| | | (A') | (a'-1) | | | | | | | | | | |
| | | (B) | (b-1) | 2 | 4 | 6 | 8 | 4 | 6 | 8 | | | |
| | | | (b-2) | | | | | | | | 4 | | |
| | | | (b-3) | | | | | | | | | 2 | 3 |
| | | (B') | (b'-1) | | | | | | | | | | |
| Ion-exchanged water | | | | Balance | Balance | Balance | Balance | Balance | Balance | Balance | Balance | Balance | Balance |
| Total | | | | 100 | 100 | 100 | 100 | 100 | 100 | 100 | 100 | 100 | 100 |
| (B)/(A) (mass ratio) | | | | 0.25 | 0.67 | 1.5 | 4.0 | 0.67 | 1.5 | 4.0 | 0.67 | 0.25 | 0.67 |
| Cleaning ratio (%) [Evaluation (I)] | | | | 29 | 30 | 30 | 29 | 27 | 28 | 29 | 27 | 29 | 30 |

TABLE 1-continued

|  |  |  |  | Examples |  |  |  |  |  | Comparative Examples |  |  |
|---|---|---|---|---|---|---|---|---|---|---|---|---|
|  |  |  |  | 1-11 | 1-12 | 1-13 | 1-14 | 1-15 | 1-16 | 1-1 | 1-2 | 1-3 |
| Liquid detergent compositions for textile products | Formulation compositions (mass %) | (A) | (a-1) | 4 | 2 | 4.5 |  | 6 | 6 | 10 |  |  |
|  |  |  | (a-2) |  |  |  |  |  |  |  | 10 |  |
|  |  |  | (a-3) |  |  | 1.5 | 6 |  |  |  |  |  |
|  |  | (A') | (a'-1) |  |  |  |  |  |  |  |  |  |
|  |  | (B) | (b-1) |  |  |  | 4 | 4 | 3.5 | 2.5 |  | 10 |
|  |  |  | (b-2) |  |  |  |  |  | 0.5 | 1.5 |  |  |
|  |  |  | (b-3) | 6 | 8 |  |  |  |  |  |  |  |
|  |  | (B') | (b'-1) |  |  |  |  |  |  |  |  |  |
| Ion-exchanged water |  |  |  | Balance | Balance | Balance | Balance | Balance | Balance | Balance | Balance | Balance |
| Total |  |  |  | 100 | 100 | 100 | 100 | 100 | 100 | 100 | 100 | 100 |
| (B)/(A) (mass ratio) |  |  |  | 1.5 | 4.0 | 0.67 | 0.67 | 0.67 | 0.67 | 0 | 0 | — |
| Cleaning ratio (%) [Evaluation (I)] |  |  |  | 28 | 27 | 29 | 27 | 30 | 28 | 25 (Reference) | 23 | 25 |

|  |  |  |  | Comparative Examples |  |  |  |  |  |  |  |
|---|---|---|---|---|---|---|---|---|---|---|---|
|  |  |  |  | 1-4 | 1-5 | 1-6 | 1-7 | 1-8 | 1-9 | 1-10 | 1-11 |
| Liquid detergent compositions for textile products | Formulation compositions (mass %) | (A) | (a-1) |  | 6 | 4 | 6 | 4 |  |  |  |
|  |  |  | (a-2) |  |  |  |  |  |  |  |  |
|  |  |  | (a-3) |  |  |  |  |  |  |  |  |
|  |  | (A') | (a'-1) | 4 | 4 | 6 |  |  |  | 6 |  |
|  |  | (B) | (b-1) | 6 |  |  |  |  |  | 2.5 | 6.25 |
|  |  |  | (b-2) |  |  |  |  |  |  | 1.5 | 3.75 |
|  |  |  | (b-3) |  |  |  |  |  | 10 |  |  |
|  |  | (B') | (b'-1) |  |  |  | 4 | 6 |  |  |  |
| Ion-exchanged water |  |  |  | Balance | Balance | Balance | Balance | Balance | Balance | Balance | Balance |
| Total |  |  |  | 100 | 100 | 100 | 100 | 100 | 100 | 100 | 100 |
| (B)/(A) (mass ratio) |  |  |  | 1.5 | 0 | 0 | 0.67 | 1.5 | — | 0.67 | — |
| Cleaning ratio (%) [Evaluation (I)] |  |  |  | 18 | 22 | 19 | 22 | 19 | 23 | 16 | 22 |

*The ratio of (IO-1S)/(IO-2S) in component (A) in Example 1-13 is 2.6

Example 2 and Comparative Example 2

For liquid detergent compositions for textile products in Example 2, the cleaning ratio was evaluated in the same manner as in Example 1 except that the hardness of water used for cleaning was changed as shown in Table 2. The results are shown in Table 2.

TABLE 2

|  |  |  |  |  | Examples |  |  |  | Comparative Example |
|---|---|---|---|---|---|---|---|---|---|
|  |  |  |  |  | 2-1 | 2-2 | 2-3 | 2-4 | 2-1 |
| Liquid detergent compositions for textile products | Formulation components (mass %) | (A) | (a-1) |  | 8 | 6 | 4 | 2 | 10 |
|  |  | (B) | (b-1) |  | 2 | 4 | 6 | 8 |  |
|  |  | Ion-exchanged water |  |  | Balance | Balance | Balance | Balance | Balance |
|  |  | Total |  |  | 100 | 100 | 100 | 100 | 100 |
|  | (B)/(A) (mass ratio) |  |  |  | 0.25 | 0.67 | 1.5 | 4.0 | 0 |
| Evaluation results | Hardness of water used for cleaning | 0° dH | Cleaning ratio 1 (%) |  | 25 | 25 | 25 | 23 | 23 |
|  |  | 8° dH | Cleaning ratio 2 (%) |  | 27 | 27 | 27 | 27 | 22 |
|  | Ratio of cleaning ratio 2/cleaning ratio 1 |  |  |  | 1.1 | 1.1 | 1.1 | 1.2 | 0.96 |

The liquid detergent compositions for textile products in Examples using component (A) and component (B) in combination are found to be superior in detergency to Comparative Example under a condition in which cleaning water has high hardness. In Examples, the detergency can be maintained without being reduced even when the hardness of cleaning water increases.

Example 3 and Comparative Example 3

Liquid detergent compositions for textile products as shown in Table 3 were obtained in the same manner as in Example 1. In Comparative Examples in Table 3, the mass ratio of (B)/(A) is shown with component (A') and component (B') used in place, respectively, of component (A) and component (B). The pH of each of the liquid detergent compositions for textile products as shown in Table 3 was measured by the pH measurement method described herein, and the results showed that all the compositions had a pH of 7.0.

For the liquid detergent compositions for textile products in Table 3, the cleaning ratio was measured in the same manner as in "Measurement of cleaning ratio" in Evaluation (I) in Example 1 except that the concentration of the liquid detergent composition for textile products, which was used for cleaning, was 0.02 mass %, and the hardness of water used for cleaning was 7° dH (evaluation in these Examples is defined as Evaluation (II)). The pH of each of the cleaning liquids was measured in accordance with the method for measuring the pH of the detergent compositions for textile products according to the present invention, and the results showed that the pH (20° C.) was 7.0. The results are shown in Table 3.

A cleaning ratio is compared against the cleaning ratio of Comparative Example 3-1, and when the value of the cleaning ratio is greater than that of Comparative Example 3-1, it can be determined that excellent detergency is exhibited. The liquid detergent compositions for textile products as described in Examples all had a cleaning ratio greater than that of the liquid detergent composition for textile products in Comparative Example 3-1. The greater the value of the cleaning ratio, the better.

TABLE 3

|  |  |  |  | Examples | | | | | | | | | |
|---|---|---|---|---|---|---|---|---|---|---|---|---|---|
|  |  |  |  | 3-1 | 3-2 | 3-3 | 3-4 | 3-5 | 3-6 | 3-7 | 3-8 | 3-9 | |
| Liquid detergent compositions for textile products | Formulation compositions (mass %) | (A) | (a-1) | 18 | 15 |  | 15 | 12.5 | 9.5 |  | 15 | 15 | |
|  |  |  | (a-2) |  |  | 15 |  |  |  |  |  |  | |
|  |  |  | (a-3) |  |  |  |  | 2.5 | 5.5 | 15 |  |  | |
|  |  | (A') | (a'-1) |  |  |  |  |  |  |  |  | 1.5 | |
|  |  | (B) | (b-1) | 2 | 5 | 5 |  | 5 |  | 5 | 2.5 | 5 | |
|  |  |  | (b-2) |  |  |  | 5 |  |  |  | 2.5 |  | |
|  |  | (B') | (b'-1) |  |  |  |  |  |  |  |  |  | |
| Ion-exchanged water |  |  |  | Balance | Balance | Balance | Balance | Balance | Balance |  | Balance | Balance | |
| Total |  |  |  | 100 | 100 | 100 | 100 | 100 | 100 | 100 | 100 | 100 | |
| (B)/(A) (mass ratio) |  |  |  | 0.11 | 0.33 | 0.33 | 0.33 | 0.33 | 0.33 | 0.33 | 0.33 | 0.33 | |
| Cleaning ratio (%) [Evaluation (II)] |  |  |  | 33 | 39 | 31 | 30 | 38 | 34 | 32 | 30 | 37 | |

|  |  |  |  | Examples | Comparative Examples | | | | | | |
|---|---|---|---|---|---|---|---|---|---|---|---|
|  |  |  |  | 3-10 | 3-1 | 3-2 | 3-3 | 3-4 | 3-5 | 3-6 | 3-7 |
| Liquid detergent compositions for textile products | Formulation compositions (mass %) | (A) | (a-1) | 15 | 20 |  |  | 12 | 15 |  |  |
|  |  |  | (a-2) |  |  | 20 |  |  |  |  |  |
|  |  |  | (a-3) |  |  |  |  |  |  |  |  |
|  |  | (A') | (a'-1) | 5 |  |  | 8 | 8 |  | 15 |  |
|  |  | (B) | (b-1) | 5 |  |  | 12 |  |  | 2.5 | 10 |
|  |  |  | (b-2) |  |  |  |  |  |  | 2.5 | 10 |
|  |  | (B') | (b'-1) |  |  |  |  |  | 5 |  |  |
| Ion-exchanged water |  |  |  | Balance | Balance | Balance | Balance | Balance | Balance | Balance | Balance |
| Total |  |  |  | 100 | 100 | 100 | 100 | 100 | 100 | 100 | 100 |
| (B)/(A) (mass ratio) |  |  |  | 0.33 | 0 | 0 | 1.5 | 0 | 0.33 | 0.33 | — |
| Cleaning ratio (%) [Evaluation (II)] |  |  |  | 35 | 27 (Reference) | 25 | 19 | 23 | 24 | 12 | 15 |

*The ratio of (IO-1S)/(IO-2S) in component (A) in Example 3-5 is 3.2.
*The ratio of (IO-1S)/(IO-2S) in component (A) in Example 3-6 is 2.1.

The invention claimed is:

1. A detergent composition for textile products, comprising the following component (A), component (B) and water:
   component (A): an internal olefin sulfonate having 16 or more and 18 or less carbons; and
   component (B): one or more anionic surfactants selected from an alkyl sulfate having 12 or more and 14 or less carbons and an alkane sulfonate having 12 or more and 14 or less carbons,
   wherein the component (A) is an internal olefin sulfonate having 16 or more and 18 or less carbons and, in the internal olefin sulfonate, a mass ratio of an internal olefin sulfonate having the sulfonate group at position 2 or higher and 4 or lower and having 16 or more and 18 or less carbons (IO-1S) to an internal olefin sulfonate having the sulfonate group at position 5 or higher and having 16 or more and 18 or less carbons (IO-2S), (IO-1S)/(IO-2S), is 0.75 or more and 5.5 or less;
   wherein a mass ratio of the content of the component (B) to the content of the component (A), (B)/(A), is 0.25 or more and 6 or less, and
   wherein the composition is used by diluting with water having a hardness of 4° dH or more in terms of German hardness and the total content of component A and the total content of component B is 1 mass % or more and 50 mass % or less.

2. The detergent composition for textile products according to claim 1, wherein the content of one or more anionic surfactants selected from an alkyl sulfate having 12 carbons and an alkane sulfonate having 12 carbons in the whole component (B) contained in the detergent composition for textile products is 50 mass % or more and 100 mass % or less.

3. The detergent composition for textile products according to claim 1, wherein the content of an internal olefin sulfonate having 16 carbons in the component (A) is 0 mass % or more and 80 mass % or less.

4. The detergent composition for textile products according to claim 1, wherein a proportion of the total amount of the component (A) and the component (B) in all surfactants contained in the detergent composition for textile products is 50 mass % or more and 100 mass % or less.

5. The detergent composition for textile products according to claim 1, wherein a proportion of the total amount of the component (A) and the component (B) in all anionic surfactants contained in the detergent composition for textile products is 50 mass % or more and 100 mass % or less.

6. A method for cleaning a textile product, comprising cleaning the textile product with a cleaning liquid in which the detergent composition for textile products according to claim 1 is diluted with water, and
   wherein the diluting water is water having a hardness of 4° dH or more in terms of German hardness.

7. The method for cleaning a textile product according to claim 6, wherein a total concentration of the component (A)

and the component (B) in the cleaning liquid is 0.001 mass % or more and 0.1 mass % or less.

8. The method for cleaning a textile product according to claim 6, wherein a pH of the cleaning liquid at 20° C. is 5 or more and 10 or less.

9. The method for cleaning a textile product according to claim 6, wherein a hardness of water for diluting the composition is 1° dH or more and 20° dH or less in terms of German hardness.

10. A method for producing a detergent composition for textile products, comprising mixing the following component (A), component (B) and water:
   component (A): an internal olefin sulfonate having 16 or more and 18 or less carbons; and
   component (B): one or more anionic surfactants selected from an alkyl sulfate having 12 or more and 14 or less carbons and an alkane sulfonate having 12 or more and 14 or less carbons,
   wherein the component (A) is an internal olefin sulfonate having 16 or more and 18 or less carbons and, in the internal olefin sulfonate, a mass ratio of an internal olefin sulfonate having the sulfonate group at position 2 or higher and 4 or lower and having 16 or more and 18 or less carbons (IO-1S) to an internal olefin sulfonate having the sulfonate group at position 5 or higher and having 16 or more and 18 or less carbons (IO-2S), (IO-1S)/(IO-2S), is 0.75 or more and 5.5 or less;
   wherein a mass ratio of the content of the component (B) to the content of the component (A), (B)/(A), is 0.25 or more and 6 or less, and
   wherein the diluting water is water having a hardness of 4° dH or more in terms of German hardness and the total content of component A and the total content of component B is 1 mass % or more and 50 mass % or less.

11. A method for improving the resistance to hardness of a detergent composition for textile products, comprising using the following component (A) and the component (B) in combination:
   component (A): an internal olefin sulfonate having 16 or more and 18 or less carbons; and
   component (B): one or more anionic surfactants selected from an alkyl sulfate having 12 or more and 14 or less carbons and an alkane sulfonate having 12 or more and 14 or less carbons,
   wherein the component (A) is an internal olefin sulfonate having 16 or more and 18 or less carbons and, in the internal olefin sulfonate, a mass ratio of an internal olefin sulfonate having the sulfonate group at position 2 or higher and 4 or lower and having 16 or more and 18 or less carbons (IO-1S) to an internal olefin sulfonate having the sulfonate group at position 5 or higher and having 16 or more and 18 or less carbons (IO-2S), (IO-1S)/(IO-2S), is 0.75 or more and 5.5 or less;
   wherein a mass ratio of the content of the component (B) to the content of the component (A), (B)/(A), is 0.25 or more and 6 or less, and
   wherein the diluting water is water having a hardness of 4° dH or more in terms of German hardness and the total content of component A and the total content of component B is 1 mass % or more and 50 mass % or less.

* * * * *